United States Patent
Zheng et al.

(10) Patent No.: US 11,896,408 B2
(45) Date of Patent: Feb. 13, 2024

(54) AUTOMATED PATIENT MODELING AND POSITIONING

(71) Applicant: Shanghai United Imaging Intelligence Co., LTD., Shanghai (CN)

(72) Inventors: Meng Zheng, Cambridge, MA (US); Abhishek Sharma, Cambridge, MA (US); Srikrishna Karanam, Cambridge, MA (US); Ziyan Wu, Cambridge, MA (US)

(73) Assignee: Shanghai United Imaging Intelligence Co., LTD., Shanghai (CN)

( * ) Notice: Subject to any disclaimer, the term of this patent is extended or adjusted under 35 U.S.C. 154(b) by 300 days.

(21) Appl. No.: 17/525,488

(22) Filed: Nov. 12, 2021

(65) Prior Publication Data

US 2023/0148978 A1    May 18, 2023

(51) Int. Cl.
*G06T 7/70* (2017.01)
*G06N 20/20* (2019.01)
*A61B 6/04* (2006.01)
*G06F 18/24* (2023.01)

(52) U.S. Cl.
CPC ............ *A61B 6/0407* (2013.01); *G06F 18/24* (2023.01); *G06N 20/20* (2019.01); *G06T 7/70* (2017.01); *G06T 2207/20084* (2013.01)

(58) Field of Classification Search
CPC .............. A61B 6/0407; G06T 7/70; G06T 2207/20084; G06N 20/20; G06F 18/24
See application file for complete search history.

(56) References Cited

U.S. PATENT DOCUMENTS

2020/0065940 A1* 2/2020 Tang ..................... G06T 3/40
2020/0375546 A1* 12/2020 Shoudy ............... A61B 5/7425

* cited by examiner

*Primary Examiner* — David P Porta
*Assistant Examiner* — Fani Polyzos Boosalis
(74) *Attorney, Agent, or Firm* — Ziegler IP Law Group

(57) ABSTRACT

Automated patient positioning and modelling includes a hardware processor to obtain image data from an imaging sensor, classify the image data, using a first machine learning model, as a patient pose based on one or more pre-defined protocols for patient positioning, provide a confidence score based on the classification of the image data and if the confidence score is less than a pre-determined value, re-classify the image data using a second machine learning model; or if the confidence score is greater than a pre-determined value, identify the image data as corresponding to a patient pose based on one or more pre-defined protocols for patient positioning during a scan procedure.

14 Claims, 5 Drawing Sheets

AUTOMATED PATIENT MODELING AND POSITIONING

FIELD

The aspects of the disclosed embodiments relate generally to patient positioning systems for medical scanning, and more particularly to a soft pose classifier for automated patient positioning and modelling.

BACKGROUND

In medical scanning procedures, such as computed tomography (CT) or Magnetic Resonance Imaging (MRI), a sensor-aided computation algorithm can help automatically position the patient for scanning. These algorithms are generally implemented in order to assist with the proper positioning of the patient for the medical scanning procedure, also referred to herein as scan or scanning.

In current automated patient positioning workflows for medical scanning, a hard or rigid classification methodology is adopted for identifying a patient pose. These rigid classification systems will set a hard threshold for prediction and generally output only one inference result among certain pre-defined options. These options might merely identify that the patient's head is towards the gantry, that the feet are towards the gantry, or that the patient is in a supine, prone or lateral position. There is no classification information or inference result that provides a more detailed analysis of the patient pose.

A rigid classification system is typically in the form of a trained deep neural network. Given the performance limitations of deep neural networks, the classification performance can be easily compromised by interference or disturbance signals in the collected sensor data or environmental changes. This can produce incorrect positioning predictions. It would be advantageous to be able to provide a soft pose classification model which considers predicted probabilities for all high-confidence classes.

Accordingly, it would be desirable to provide methods and apparatus that address at least some of the problems described above.

SUMMARY

The aspects of the disclosed embodiments are directed to a method, apparatus and system for automated patient positioning and modelling. This and other advantages of the disclosed embodiments are provided substantially as shown in, and/or described in connection with at least one of the figures, as set forth in the independent claims. Further advantageous modifications can be found in the dependent claims.

According to a first aspect, the disclosed embodiments provide a method for automated patient positioning and modelling. In one embodiment, the method includes obtaining, by a hardware processor, image data from a sensor. The obtained image data is classified as a patient pose using a first machine learning model. A confidence score of the patient pose is provided based on the classification of the image data. If the confidence score is less than a pre-determined value, the image data is re-classified using a second machine learning model. If the confidence score is greater than a pre-determined value, the image data is identified as a patient pose corresponding to one or more predefined protocols for patient positioning. The aspects of the disclosed embodiments are configured to determine whether the patient pose on the gantry, for example, is consistent with one or more pre-defined protocols for a scanning procedure.

In a possible implementation form, the first machine learning model can be or is an ensemble model and the second machine learning model can be or is a deep convolutional neural network model.

In a possible implementation form, the image data is patient pose image data.

According to a second aspect the disclosed embodiments provide a system for automated patient positioning and modelling. In one embodiment, the system includes one or more imaging sensors and a hardware processor. The hardware processor is configured to receive image data from the one or more imaging sensors. The hardware processor is further configured to classify the image data, using a first machine learning model, as a patient pose based on one or more pre-defined protocols for patient positioning. The hardware processor will provide a confidence score based on the classification of the image data. If the confidence score is less than a pre-determined value, the hardware processor will re-classify the image data using a second machine learning model. If the confidence score is greater than a pre-determined value, the hardware processor will identify the image data as corresponding to a correct patient pose based on the one or more pre-defined protocols for patient positioning.

According to a third aspect the disclosed embodiments are directed to a computer program product. In one embodiment, the computer program product has a non-transitory computer-readable medium with machine-readable instructions stored thereon. The execution of the machine-readable instructions by a computer will cause the computer to obtain image data from a sensor and classify the image data using a first machine learning model as a patient pose. A confidence score is provided based on the classification of the image data. If the confidence score is less than a pre-determined value, the image data is re-classified using a second machine learning model. If the confidence score is greater than a pre-determined value, the image data is identified as a patient pose corresponding to one of a correct patient pose.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings, in which.

DETAILED DESCRIPTION OF THE DISCLOSED EMBODIMENTS

The following detailed description illustrates exemplary aspects of the disclosed embodiments and ways in which they can be implemented. Although some modes of carrying out the aspects of the disclosed embodiments have been disclosed, those skilled in the art would recognize that other embodiments for carrying out or practising the aspects of the disclosed embodiments are also possible.

Figure 1:
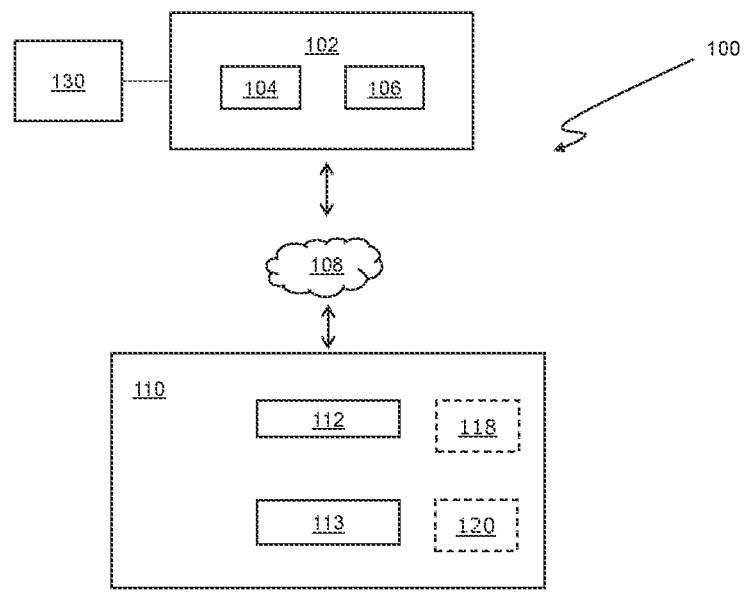
FIG. 1 is a network environment diagram of an exemplary system for automated patient positioning and modelling in accordance with the aspects of the disclosed embodiments.

Referring to FIG. 1, a schematic block diagram of an exemplary system 100 for automated patient position and modelling is illustrated. The aspects of the disclosed embodiments are generally directed to automatically identifying patient poses prior to an imaging or scanning procedure and determining whether the patient pose is aligned with the required scanning protocols, referred to herein as pre-defined protocols. The soft pose classification system of the disclosed embodiments is intended to be implemented in different medical imaging environments, including, but not limited to CT, X-Ray and MRI.

As shown in FIG. 1, the system 100 generally includes a computing device or server 102. Although a server is generally referred to herein, the aspects of the disclosed embodiments are not so limited. In alternate embodiments, the server 102 can include any suitable computer or computing arrangement.

In one embodiment, the server 102 includes a processor 104, such as a hardware processor. Although only one processor 104 is generally described herein, the aspects of the disclosed embodiments are not so limited. In alternate embodiments, the server 102 can include any suitable number of processors 104.

The system 100 is generally configured to take an image as the input data, which is obtained from one or more imaging or optical sensors 112. In one embodiment, the hardware processor 104, either alone or in combination with other components of the system 100, is generally configured to obtain the input data, the images or image data, from one or imaging sensor(s) 112 disposed in an imaging room 110. The processor 104 is configured to classify the image data, using a first machine learning model, also referred to as pose inference module 106, as a patient pose. The label for the patient pose will generally be based on one or more pre-defined protocols for patient positioning during or in conjunction with a scanning or imaging procedure.

A confidence score is then provided by the pose inference model 106 based on the classification of the image data by the pose inference model 106. The confidence score reflects the assessment by the pose inference model 106 that the prediction corresponds to the indicated pose position label. Examples of such pose position labels, include, but are not limited to "supine feet toward gantry", "prone feet toward gantry" or "prone head toward gantry." These are merely examples and are not intended to limit the scope of the claimed subject matter.

If the confidence score is less than a pre-determined value, meaning that the pose inference model 106 cannot reliably determine or identify the pose from the image data, the hardware processor 104 is configured to re-classify the image data using a second machine learning model. In one embodiment, the second machine learning model can be or is a deep convolutional neural network model.

If the confidence score is greater than a pre-determined value, meaning that the pose inference model 106 has determined that the image data corresponds to a certain pose, the image data is identified or otherwise labelled as corresponding to a patient pose based on one or more pre-defined protocols for patient positioning.

In one embodiment, the apparatus or system 100 can also include a user interface 130. The user interface 130 can be communicatively coupled to the server 102 and is configured to provide an output of the pose predictions, as is generally described herein. For example, in one embodiment, the user interface 130 can provide a list of the top "n" predictions of the pose inference model 106.

Generally, the automated patient positioning and modelling will be implemented and carried out in an imaging room 110, such as in a hospital or medical facility. In one embodiment, the imaging area or room 110 is a medical scanning or imaging room where medical imaging is performed. The aspects of the disclosed embodiments can be implemented in any suitable medical imaging environment, including, but not limited to, CT, MRI and X-Ray, for example.

The imaging room 110 will generally include at least one image capture device 112, and an imaging platform 114, also referred to as a gantry. The image capture device 112, which might also be referred to as a camera, will generally comprise an image or optical sensor. Examples of suitable sensors include, but are not limited to, red-blue-green sensors, depth sensors, a digital camera, an image sensor, a night vision capable camera, a video recorder, a CCTV camera, and other types of image-capture devices. In alternate embodiments, any suitable image sensor or device can be used to capture patient pose information.

The image capture device(s) 112 are disposed or installed at specific location(s) within the imaging area 110 to adequately capture images of a patient, also referred to herein as poses, on the imaging platform 114. In one embodiment, the image capture device 112 is installed on or in connection with a ceiling of the imaging room 110. In this manner, the imaging platform 114, and the patient that is disposed on or in connection with the imaging platform 114, is within a field of view 116 of the image capture device 112. Although the description here is generally with respect to the ceiling of the imaging room, the aspects of the disclosed embodiments are not so limited. In alternate embodiments, the image sensor 112 or camera can be located at or in connection with any suitable location in the room, including for example, the sidewalls or on the imaging device itself. The aspects of the disclosed embodiments are generally directed to providing a readiness check of the patient positioning before or as the patient is sent into the gantry.

Figure 2:
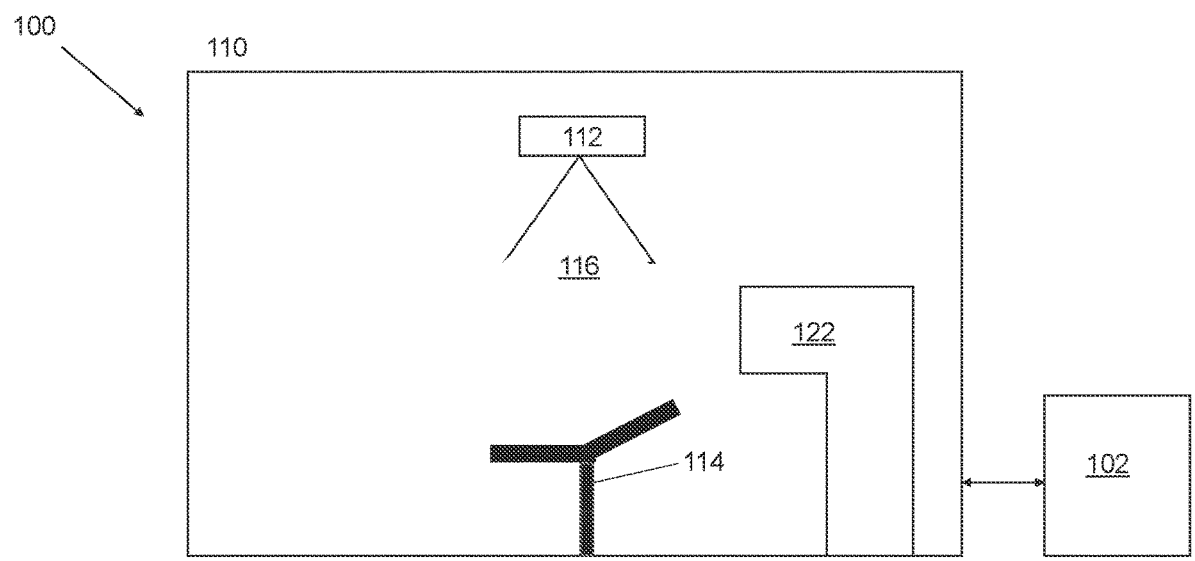
FIG. 2 is a schematic illustration of an exemplary scenario for implementation of a system for automated patient positioning and modelling incorporating aspects of the disclosed embodiments.

FIG. 2 illustrates an exemplary implementation of a system 100 incorporating aspects of the disclosed embodiments. In this example, a patient platform 114 is disposed in an imaging room 110. An image sensor(s) 112 is disposed in the room 110, which in this example is above the patient platform 114, such as on the ceiling. The image sensor 112 is disposed so that the patient platform 114 is disposed within the field of view 116 of the image sensor 112. An exemplary gantry 122 is disposed in conjunction with patient platform 114. The server 102 is communicably coupled to the image sensor 112 and is configured to receive the captured image data as an input.

In the example of FIG. 2, the image sensor 112 is disposed on the ceiling of the imaging room 110. The field of view 116 of the image capture device 112 will generally encompass a wide area, including for example, the scanner platform or gantry 114. Generally, the patient might be lying down during the image capture process. Alternatively, the patient could be sitting or in some other position for the image capture process. The aspects of the disclosed embodiments are not intended to be limited by the particular position of the patient during the image capture process.

For each scanning case, a patient first arrives at the medical scanning room 110 and enters into the field of view 116 of the image sensor(s) 112. The patient is then positioned on the patient platform or scanner bed 114 and prepares for the scanning. This positioning can be implemented in any suitable manner. The patient can lie down or sit, or take any suitable position needed for the scanning. In one embodiment, an off-the-shelf person detection algorithm can be applied to determine if the patient is roughly positioned in the field of view 116 of the sensor 112.

In one embodiment, once it is detected that the patient is in a suitable position with respect to the imaging platform 114, such as for example, lying down, the image sensor(s) 112 will capture images, or pose positions, of the patient. Generally, the images will be captured with respect to gantry 114. This can include for example, capturing images of pre-defined positions that correspond to joint locations of the patient. In one embodiment, the sensor or image data can be transmitted to the processor 104 and the pose inference model 106 for pose inference, as is described herein.

Instead of rigid classification, which outputs only one inference result among certain pre-defined options, the pose inference model 106 of the disclosed embodiments is configured to consider all possible positions which achieve high probability predictions. The pose inference model 106 of the disclosed embodiments will then output the top "n" predictions along with a computed confidence score, based on classifier prediction to the user.

For example, a first pose image, pose 1, (supine feet toward gantry) receives 0.4 as confidence score. A second pose image, pose 2 (prone feet toward gantry) receives 0.9 as a confidence score. The nth pose image, pose n (prone head toward gantry) receives a 0.004 as the confidence score. As will generally be understood, any suitable number of pose images can be captured.

In one embodiment, the apparatus 100 is configured to provide a list of the confidence scores to the user. The list can be presented, for example, on or via the user interface 130 of the apparatus 100.

In one embodiment, the list of confidence scores above can be ranked with the top scores appear first. For the example above, the scores are listed in the following order: 1) pose 2 (prone feet toward gantry), 2) pose 1 (supine feet toward gantry), . . . , n) pose n (prone head toward gantry). In this manner, the user, such as a technician, can choose or otherwise confirm any one of these options by also looking at the real patient pose.

The user in this example, typically a technician, can use the list of the top "n" predictions to either confirm the patient positioning prior to the imaging process, or re-position the patient. In one embodiment, the option list contains the correct patient pose so that the technician can manually choose the correct pose. The real or actual patient pose may not be aligned with the pose required for the pre-defined protocols.

The system 100 is configured to check if the chosen pose is aligned with pre-defined protocols which require a certain pose for medical scanning and provide instructions accordingly. The aspects of the disclosed embodiments provide a more user friendly positioning system that was previously realized.

In one embodiment, if the prediction output of the pose inference model 106 does not align with the predefined protocol, rather than just a warning message, the system 100 is configured to output one or more high confidence predictions based on a soft threshold. The confidence prediction(s) can be presented to the technician on a suitable user interface. The technician can choose from the one or more confidence predictions. After the technician makes the choice, the system 100 will first compare the current pose of the patient as confirmed by the user and the pre-defined scanning protocols. The system 100 will then provide instructions for the patient to adjust his/her pose. The instructions, which can be provided verbally or displayed on a screen installed in the medical scanning room are based on the difference(s) between the current patient pose and the predefined patient poses. This can avoid complicated and redundant operation, such as confirming the warning message and then manually making an adjustment to correct the patient pose.

The aspects of the disclosed embodiments will provide possible options for user to choose from. For example, the system 100 is configured to present several options of the possible patient poses with decreasing possibilities, such as for example, 1) supine feet towards gantry or 2) lateral feet towards gantry. The user will be asked to choose from one of these options. The system 100 then checks whether the user choice, which should reflect the actual patient pose and the pose required by the predefined protocol, align. If there is alignment between the user choice and the pose of the predefined protocol, the system 100 can initiate the scanning process. If the user choice does not align with the pose required by the predefined protocol, the system 100 is configured to inform one or both of the technician and patient. In this manner, further pose adjustment can take place until the system 100 confirms that the patient pose is correct for the scanning.

The aspects of the disclosed embodiments facilitate online model learning for more accurate model performance. For example, if the technician chooses a pose that is different from the model prediction, this means that the original prediction from the pose inference model 106 is not correct. The pose inference model 106 can take new data, such as the 2D keypoint data, sensor data collected from image capture device 112, the pose label from the technician, and the original wrong prediction, for further online learning/fine-tuning of the pose inference model 106, such as by reinforcement learning.

In the typical patient positioning system with hard pose identification, the system will show warning messages if the predicted patient pose does not align with pre-defined scanning protocol. The technician then needs to manually confirm or bypass the warning message, and manually correct the model prediction if it is incorrect. In soft pose identification process of the disclosed embodiment, this situation will be alleviated, even if the model 106 is not confident about the prediction.

Rather than providing warning messages, the aspects of the disclosed embodiments present options to the user, generally through the user interface 130. In this manner, the aspects of the disclosed embodiments allow the user to directly choose the correct pose when the model 106 is not confident about its own prediction. This can be more efficient and user-friendly as compared to hard pose cases, which only issue warnings.

In one embodiment, the aspects of the disclosed embodiments enable the user(s) to input the ground-truth pose information with one click. For example, as also described above, the provided option list will include the correct patient pose. The technician can manually choose the correct that pose option that reflects the real patient pose by "clicking" the selection on the user interface 130. The system 100 is configured to check if the selected pose is aligned with the pose required for the pre-defined protocols. The system 100, and in particular the pose inference model 106, will then be corrected/updated given the user input. By incorporating user-in-the-loop fashion in the system 100, the pose inference model 106 of the disclosed embodiments can be updated and perform increasingly better.

Figure 3:
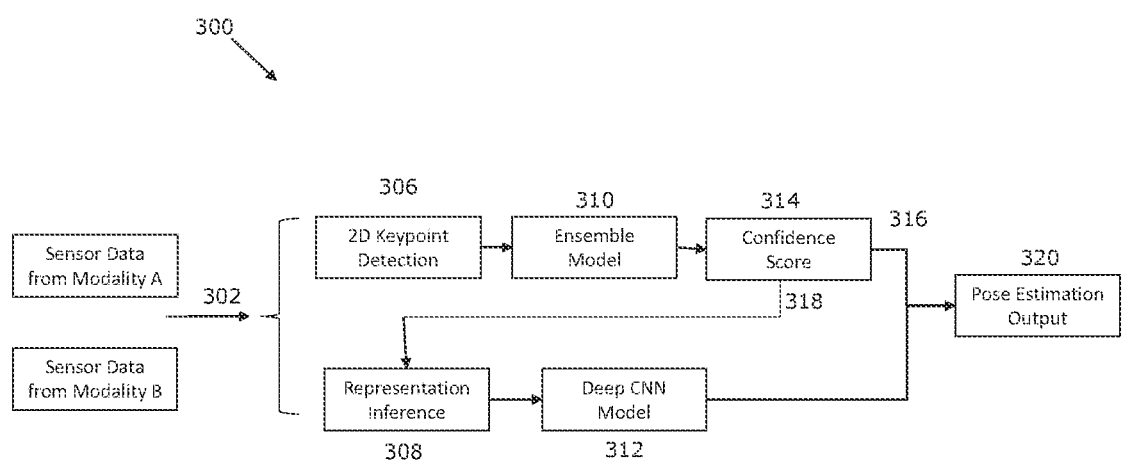
FIG. 3 is a process flow diagram illustrating aspects of the automated patient positioning and modelling of the disclosed embodiments.

FIG. 3 illustrates an exemplary flow diagram of a workflow 300 incorporating aspects of the disclosed embodiments. In this example, sensor data from the image sensor 112 of FIG. 1, is acquired 302 from one or both of Modality A and Modality B, where modality refers to different types of imaging sensors 112. Examples of the different modalities can include, but are not limited to, digital cameras, camera modules, camera phones, optical mouse devices, medical imaging equipment, night vision equipment such as thermal imaging devices, and others.

In one embodiment, a two dimensional key point detection (2D Key point Detection) 306 is used to verify the image data as joint location images. Generally, 2D Key point Detection is used to acquire images of pre-determined joint locations. For example, an image of the patient in the field of view 116 of FIG. 2 is captured by a camera. The image is then processed using a 2D Key point Detection algorithm to detect and/or identify pre-determined joints or joint locations.

The output of the 2D Key point Detection 306, the 2D joint locations of the predefined body joints, is provided to a first machine learning algorithm 310. In one embodiment, the first machine learning algorithm 310 is an ensemble model. In alternate embodiments, the first machine learning algorithm 310 can comprise any suitable machine learning model that 2D body keypoint locations as inputs and outputs classification probability predictions. The training typically optimizes model parameters given certain amount of training data. In one embodiment, the training data includes pairs of 2D keypoint joint locations and the corresponding pose class labels.

The ensemble model 310 is configured to generate a classification or confidence score 314 that is associated with the sensor image data. In one embodiment, the confidence score 314 is normalized from 0 to 1, where a score of 0 is associated with a low confidence and a score of 1 is associate with a high confidence. A low confidence score is assigned when the model 310 is not confident that the patient is in the correct position or pose for the imaging. A low confidence score does not mean that the pose of the patient is incorrect. Rather, the low confidence score can imply that the model 310 was not able to determine that the pose is correct.

A high confidence score is assigned 316 when the model 310 is confident that the patient is in the correct position for the particular imaging process. In other words, a high confidence score is assigned when the model 310 is confident about its own prediction. While, in the unlikely situation that the model prediction may is not correct, even with a high confidence score, system 100 is configured to allow the technician to manually intervene and correct the prediction of the model 310.

If the confidence score indicates a high confidence 316 in the prediction, a pose estimation output 320 is provided. The output 320 will be a class label indicating which pose the patient is currently in. An example of such a label is "supine with feet towards gantry." The system 100 is configured to check whether this label aligned with the selected protocol. For example, chest CT requires the patient to be in the "supine feet towards gantry pose." If the output 320 in this example is the label "supine feet towards gantry pose", the output 320 of pose estimation confirms the patient pose is correct and then the system 100 will start the corresponding scanning process.

If the confidence score indicates a low confidence 318, meaning that the model 310 is not confident the patient is in a certain pose, the input data 302 is processed by a second machine learning model 312. In this example, the second machine learning model is a more detailed and extensive machine learning model. One example of such a model is a deep convolutional neural network. The second machine learning model will generally have been trained on a much larger training set than the first machine learning model. The second machine learning model will also be more time and resource intensive, requiring more inference and memory. The output of the second machine learning module 312 will be the pose estimation output 320. In one embodiment, the output 320 can provide the possible patient pose predictions in decreasing possibilities, such as "1) supine feet towards gantry" or "2) lateral feet towards gantry." The user can then choose from one of these options to initiate the corresponding scanning process.

In one aspect, the disclosed embodiments include a training phase and an operational phase. In the training phase, the pose model 106 is trained, using training data, to enable the pose model 106 to perform specific intended functions in the operational phase. The processor 104 is configured to execute supervised training of the pose model 106 using training data of images of the pre-defined pose or joint positions to obtain a trained pose model 106. The training data contains pairs of sensor data with labeled pose annotation, or pairs of 2D keypoint locations with labeled pose annotation.

As an example, during the training of the pose model 106, images, for example normal 2D images, of pre-defined joint positions and some images with abnormality are fed to the pose model 106. Initially, the pose model 106 is not provided with information about where the abnormality is present in the images having abnormality. The pose model 106 is configured to automatically finds the abnormality in the images. The term "abnormality" refers to deviation in following the defined set of protocols and procedures while performing a specific task. For example, in an image a joint may be detected at a location which may be not correspond to its designated location.

In accordance with an embodiment, the training data includes images, or a sequence of images, provided by image-capture devices to the server 102. Optionally, the training data of images of the pre-defined joint locations is pre-stored in the server 102. Based on the training of the pose model 106, a trained pose model is obtained which is used in the operational stage of the system 100.

In operation, the processor 104 is configured to obtain the pose image(s) from the image-capture device(s) 112. The processor 104 receives the image(s) via the communication network 108. In one embodiment, the image(s) is obtained in real time or near-real time as such images are captured. Optionally, an image has a time stamp associated therewith. In an embodiment, the server 102 is configured to store information about a location associated with each of the plurality of image-capture devices 112.

In one embodiment, the processor 104 is configured to communicate an alert together with visual information, to a specified electronic device, such as a smartphone or other portable device, that is mapped or otherwise communicatively coupled to a user, such as a technician. The alert is communicated based on the pose estimation output 320. The visual information is a visual explanation indicative of a reason of the alert. The alert together with visual information is communicated as a part of the action associated the pose estimation output.

As an example, in a hospital environment, the processor 104 communicates the alert together with visual information to a smartphone of a hospital personnel, such as a doctor or a lab assistant. The hospital personnel may be associated with a specific location, such as an MRI room in case the abnormality is detected in the MRI room.

The electronic device may include, but is not limited to a cellular phone, personal digital assistants, handheld devices, wireless modems, laptop computers, personal computers and the like. The electronic devices can be mapped with registered users and communicatively coupled to the processor 104.

In another implementation, the processor 104 is further configured to communicate an instruction to a suitably configured medical device equipment or technician. In one embodiment, the instruction is communicated based on the pose estimation output.

Figure 4:
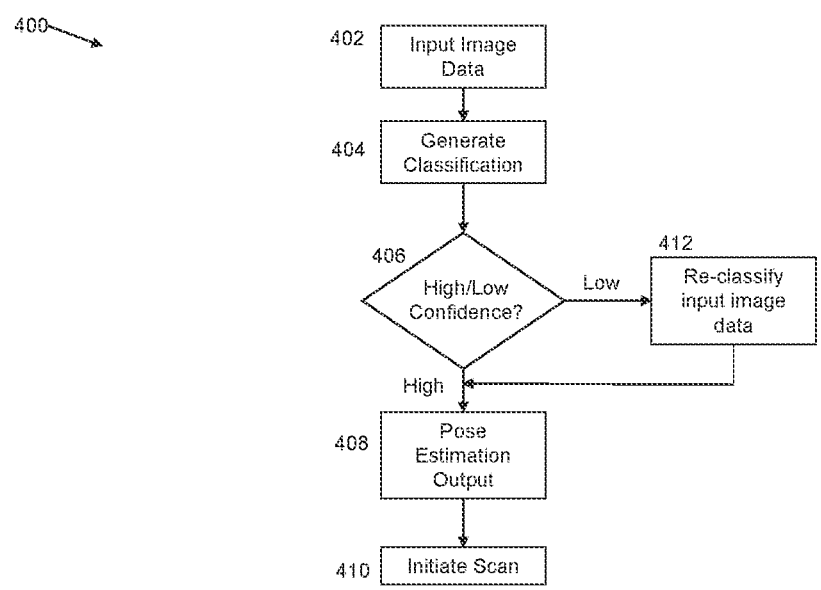
FIG. 4 is a flowchart illustrating a method incorporating aspects of the disclosed embodiments.

FIG. 4 illustrates one embodiment of a method 400 incorporating aspects of the disclosed embodiments. In this example, an image(s) corresponding to a pose is taken as the input data 402. As described above, the image, or images, are captured by suitable image capture devices. The pose image input data is then classified 404 using a machine learning model. The machine learning model of the disclosed embodiments is configured to automatically identify patient poses from the input image data and determine if the input image data is aligned with required scanning protocols.

It is determined 406 whether a confidence score associated with the classification is a high score or a low score. A high score is generally associate with a high probability prediction that the input image data is aligned with the required scanning protocol. A low score indicates a low probability prediction that the input image data is aligned with the required scanning protocol.

If the confidence score is a high score, a pose estimate output is provided 408. The pose estimation output provides the top "n" predictions along with the confidence score based on the classifier prediction. The user, such as a technician, can make a choice from the several high confidence predictions and initiate 410 the scan.

If the confidence score is a low score, the pose inference model of the disclosed embodiments cannot reliably determine or identify the pose from the input image data. In this case, the input image data is reclassified 412 using a second machine learning model. The second machine learning model is generally a more intensive and complicated classification model, such as a deep convolutional neural network model.

Referring again to FIG. 1, the server 102 generally includes suitable logic, circuitry, interfaces and/or code that is configured to receive one or more pose images from the image-capture device(s) 112 and process those images as is generally described herein. In some embodiments, the server 102 can be configured to receive a sequence of image frames (e.g. one or more video) of the patient from the image-capture device(s) 112. Examples of the server 102 may include, but are not limited to, an application server, a web server, a database server, a file server, a cloud server, or a combination thereof.

The processor 104 generally includes suitable logic, circuitry, interfaces and/or code that is configured to process the image(s) (or the sequence of image frames) as is generally described herein. In one embodiment, this can also include the pose module 106. The processor 104 is configured to respond to and process instructions that drive the system 100. Examples of the processor 104 include, but are not limited to, a microprocessor, a microcontroller, a complex instruction set computing (CISC) microprocessor, a reduced instruction set (RISC) microprocessor, a very long instruction word (VLIW) microprocessor, or any other type of processing circuit. Optionally, the processor 104 may be one or more individual processors, processing devices and various elements associated with a processing device that may be shared by other processing devices. Additionally, the one or more individual processors, processing devices and elements are arranged in various architectures for responding to and processing the instructions that drive the system 100. Although a server and hardware processor are generally described herein, the aspects of the disclosed embodiments are not so limited. In alternate embodiments, the system 100 can include any suitable components or devices that are needed to carry out the processes described herein, such as a memory or storage, for example.

In one embodiment, the patient pose model 106 can comprise or be part of a standalone computing device, in communication with, or part of, the hardware processor 104. In one embodiment, the patient pose model 106 will include or be connected to the machine learning models needed to carry out the aspects of the disclosed embodiments described herein.

In one embodiment, the server 102 is communicatively coupled to the image capture device(s) 112 via the communication network 108. The communication network 108 includes a medium through which the image-capture device(s) 112 and the server 102 communicate with each other. The communication network 108 may be a wired or wireless communication network. Examples of the communication network 108 may include, but are not limited to, a Wireless Fidelity (Wi-Fi) network, a Local Area Network (LAN), a wireless personal area network (WPAN), a Wireless Local Area Network (WLAN), a wireless wide area network (WWAN), a cloud network, a Long Term Evolution (LTE) network, a plain old telephone service (POTS), a Metropolitan Area Network (MAN), and/or the Internet. The image-capture device(s) 112 are configured to connect to the communication network 108, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, Long Term Evolution (LTE), Light Fidelity (Li-Fi), and/or other cellular communication protocols or Bluetooth (BT) communication protocols, including variants thereof. Optionally or in addition to, one or more medical equipment or device(s) 118 and/or medical imaging device(s) 120 are communicatively coupled to the server 102.

Figure 5:
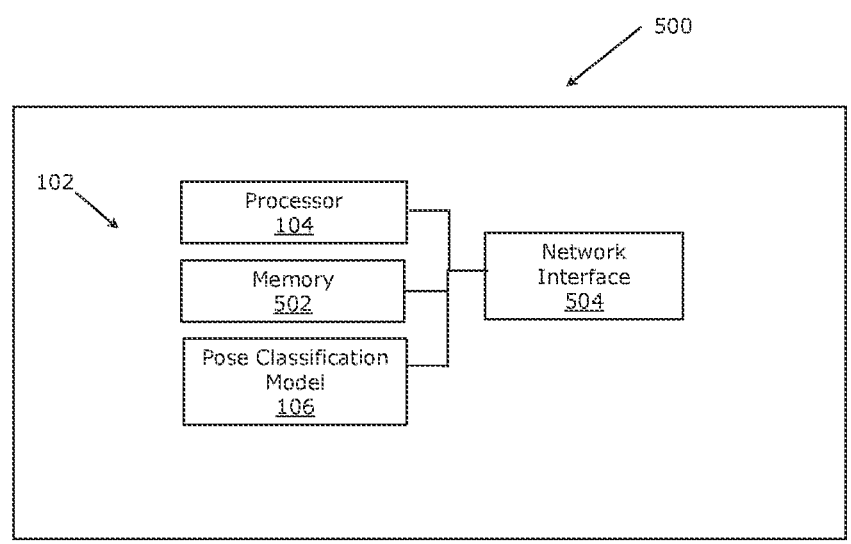
FIG. 5 is a block diagram of exemplary components of a server architecture for automated patient positioning and modelling in accordance with the aspects of the disclosed embodiments.

FIG. 5 is a block diagram 500 of exemplary components of a server for automated patient positioning in accordance with the aspects of the disclosed embodiments. FIG. 2 is described in conjunction with elements from FIG. 1. With reference to FIG. 1, there is shown the server 102. In this example, the server 102 includes a memory 402, a network interface 504, the processor 104, and the pose classification model 106. The processor 104 is communicatively coupled to the memory 402, the network interface 504, and the pose classification model 106.

The memory 502 may comprise suitable logic, circuitry, interfaces, and/or code that may be configured to store instructions executable by the processor 104. The memory 502 is further configured to store the image(s) from the image sensor 112. The memory 502 may be further configured to store operating systems and associated applications of the server 102 including the pose classification model 106. Examples of implementation of the memory 502 may include, but are not limited to, Random Access Memory (RAM), Read Only Memory (ROM), Hard Disk Drive (HDD), Flash memory, and/or a Secure Digital (SD) card. A computer readable storage medium for providing a non-transient memory may include, but is not limited to, an electronic storage device, a magnetic storage device, an optical storage device, an electromagnetic storage device, a semiconductor storage device, or any suitable combination of the foregoing.

The network interface 504 includes suitable logic, circuitry, and/or interfaces that is configured to communicate with one or more external devices, such as the image-capture device(s) 112, the medical equipment 118, 120 or an electronic device (such as a smartphone) shown in FIG. 1. Examples of the network interface 504 may include, but is not limited to, a radio frequency (RF) transceiver, an antenna, a telematics unit, one or more amplifiers, one or more oscillators, a digital signal processor, a coder-decoder (CODEC) chipset, and/or a subscriber identity module (SIM) card. Optionally, the network interface 404 may communicate by use of various wired or wireless communication protocols.

The aspects of the disclosed embodiments are directed to a soft pose classification model based on deep/machine learning algorithms that can be directly integrated into any existing patient positioning system workflow. The model, along with its associated system, is able to automatically identify or predict patient poses and check if they are aligned with requiring scanning protocols. The system of the disclosed embodiments outperforms existing state-of-the-art systems and is robust to adversarial attacks, which is a well-known potential risk for most of existing deep learning-based models and systems.

Various embodiments and variants disclosed above, with respect to the aforementioned system 100, apply mutatis mutandis to the method. The method described herein is computationally efficient and does not cause processing burden on the processor 104.

Modifications to embodiments of the aspects of the disclosed embodiments described in the foregoing are possible without departing from the scope of the aspects of the disclosed embodiments as defined by the accompanying claims. Expressions such as "including", "comprising", "incorporating", "have", "is" used to describe and claim the aspects of the disclosed embodiments are intended to be construed in a non-exclusive manner, namely allowing for items, components or elements not explicitly described also to be present. Reference to the singular is also to be construed to relate to the plural.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for automated patient positioning and modelling, the method comprising using a hardware processor to:
    obtain image data from an imaging sensor;
    classify the image data, using a first machine learning model, as a patient pose based on one or more pre-defined protocols for patient positioning;
    provide a confidence score based on the classification of the image data; and
        if the confidence score is less than a pre-determined value, re-classify the image data using a second machine learning model; or
        if the confidence score is greater than a pre-determined value, identify the image data as corresponding to a patient pose based on the one or more pre-defined protocols for patient positioning.

2. The method according to claim 1 further comprising initiating a scan corresponding to the one or more pre-defined protocols for patient positioning when the image data is identified as corresponding to the patient pose based on the one or more pre-defined protocols for patient positioning.

3. The method according to claim 1 wherein the first machine learning model is an ensemble model and the second machine learning model is a deep convolutional neural network model.

4. The method according to claim 1, wherein the image data is patient pose image data.

5. The method according to claim 1, further comprising providing a ranking of confidence scores and enabling a selection of a pose associated with a confidence score.

6. The method according to claim 5, further comprising comparing the selected pose to a required pose of the pre-defined protocol; and
    confirming the selected pose as corresponding to the pose of the pre-defined protocol and beginning the scan; or
    provide pose adjustment instructions if the selected pose is not confirmed.

7. A system for automated patient positions and modelling, comprising:
an imaging sensor; and
a hardware processor configured to receive image data from the imaging sensor, wherein the hardware processor is further configured to:
classify the image data, using a first machine learning model, as a patient pose based on one or more pre-defined protocols for patient positioning;
provide a confidence score based on the classification of the image data; and
if the confidence score is less than a pre-determined value, re-classifying the image data using a second machine learning model; or
if the confidence score is greater than a pre-determined value, identify the image data as corresponding to a patient pose based on the one or more pre-defined protocols for patient positioning.

8. The system according to claim 7, wherein the hardware processor is further configured to initiate a scan corresponding to the one or more pre-defined protocols for patient positioning when the image data is identified as corresponding to the patient pose based on the one or more pre-defined protocols for patient positioning.

9. The system according to claim 7, wherein the first machine learning model is an ensemble model and the second machine learning model is a deep convolutional neural network model.

10. The system according to claim 7, wherein the image data is patient pose image data.

11. The system according to claim 7, wherein the hardware processor is further configured to output via a user interface a ranking of confidence scores and enable a selection of a pose associated with a confidence score.

12. The system according to claim 11, wherein the hardware processor is further configured to compare the selected pose to a required pose of the pre-defined protocol; and
confirm the selected pose as corresponding to the pose of the pre-defined protocol and begin the scan; or
provide pose adjustment instructions if the selected pose is not confirmed.

13. A computer program product comprising a non-transitory computer-readable medium having machine-readable instructions stored thereon, which when executed by a computer causes the computer to:
obtain image data from an imaging sensor;
classifying the image data, using a first machine learning model as a patient pose based on one or more pre-defined protocols for patient positioning;
providing a confidence score based on the classification of the image data; and
if the confidence score is less than a pre-determined value, re-classifying the image data using a second machine learning model; or
if the confidence score is greater than a pre-determined value, identify the image data as corresponding to a patient pose based on the one or more pre-defined protocols for patient positioning.

14. The computer program product according to claim 13, further comprising execution of the machine-readable instructions by the computer to automatically begin a scan according to the one or more pre-defined scanning protocol when the correct patient pose is selected.

* * * * *